United States Patent
Esenaliev

(10) Patent No.: US 9,504,824 B2
(45) Date of Patent: Nov. 29, 2016

(54) NONINVASIVE THERAPIES IN THE ABSENCE OR PRESENCE OF EXOGENOUS PARTICULATE AGENTS

(75) Inventor: Rinat O. Esenaliev, League City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 589 days.

(21) Appl. No.: 12/821,398

(22) Filed: Jun. 23, 2010

(65) Prior Publication Data

US 2011/0034855 A1 Feb. 10, 2011

Related U.S. Application Data

(60) Provisional application No. 61/219,693, filed on Jun. 23, 2009, provisional application No. 61/322,515, filed on Apr. 9, 2010.

(51) Int. Cl.

| | |
|---|---|
| *A61M 31/00* | (2006.01) |
| *A61N 1/32* | (2006.01) |
| *A61M 37/00* | (2006.01) |
| *A61N 1/30* | (2006.01) |
| *A61N 2/00* | (2006.01) |

(52) U.S. Cl.
CPC .......... *A61N 1/325* (2013.01); *A61M 37/0092* (2013.01); *A61N 1/30* (2013.01); *A61N 2/002* (2013.01)

(58) Field of Classification Search
CPC ........ A61N 5/062; A61N 1/327; A61N 7/00; A61N 1/328; A61N 5/00; A61N 1/30; A61N 1/325; A61N 2/002; A61M 37/0092

USPC .......................................................... 604/501
See application file for complete search history.

(56) References Cited

U.S. PATENT DOCUMENTS

| | | | |
|---|---|---|---|
| 4,566,454 A * | 1/1986 | Mehl et al. ...................... 606/36 |
| 5,304,170 A * | 4/1994 | Green ............................... 606/9 |
| 6,165,440 A | 12/2000 | Esenaliev |
| 6,344,272 B1 | 2/2002 | Oldenburg |
| 6,428,811 B1 | 8/2002 | West et al. |
| 6,530,944 B2 | 3/2003 | West |
| 6,645,517 B2 | 11/2003 | West |
| 6,660,381 B2 | 12/2003 | Halas |
| 6,685,730 B2 * | 2/2004 | West .................. A61K 41/0052 607/100 |
| 6,685,986 B2 | 2/2004 | Oldenburg |
| 6,699,724 B1 | 3/2004 | West |
| 6,778,316 B2 | 8/2004 | Halas |
| 6,852,252 B2 | 2/2005 | Halas |
| 6,908,496 B2 | 6/2005 | Halas |
| 6,945,937 B2 | 9/2005 | Culp et al. |
| 7,144,627 B2 | 12/2006 | Halas |

(Continued)

OTHER PUBLICATIONS

CDC Niosh Pocket Guide to Chemical Hazards: dichlorotetrafluoroethane. Aug. 21, 2012.

(Continued)

*Primary Examiner* — Jason Flick
(74) *Attorney, Agent, or Firm* — Blank Rome LLP

(57) ABSTRACT

Methods are disclosed for treating cell components, cells, organelles, organs, and/or tissues with acoustic energy, electromagnetic energy, static or alternating electric fields, and/or static or alternating magnetic fields in the presence or absence of exogenous particulate agents for therapeutic applications.

15 Claims, 18 Drawing Sheets

(56) References Cited

U.S. PATENT DOCUMENTS

| | | | |
|---|---|---|---|
| 7,232,431 | B1 | 6/2007 | Weimann |
| 7,358,226 | B2 | 4/2008 | Dayton et al. |
| 7,367,934 | B2 * | 5/2008 | Hainfeld ............ A61K 41/0038 600/1 |
| 7,824,395 | B2 * | 11/2010 | Chan et al. ..................... 606/10 |
| 7,993,331 | B2 | 8/2011 | Barzilay et al. |
| 2003/0059386 | A1 | 3/2003 | Sumian |
| 2003/0129154 | A1 | 7/2003 | McDaniel |
| 2004/0006328 | A1 * | 1/2004 | Anderson ..................... 604/501 |
| 2006/0241524 | A1 | 10/2006 | Lee et al. |
| 2007/0078290 | A1 | 4/2007 | Esenaliev |
| 2009/0306646 | A1 * | 12/2009 | Turner ............... A61B 18/1815 606/33 |

OTHER PUBLICATIONS

CDC Niosh Pocket Guide to Chemical Hazards: dichlorodifluormethane. Aug. 21, 2012.

Dupont Freon 114 MSDS: Jan. 1, 1997.

CDC Niosh Pocket Guide to Chemical Hazards: 1,1,1,2-tetrafluoroethane. Oct. 12, 2012.

Chumakova OV et al "Composition of PLGA and PEI/DNA nanoparticles improves ultrasound-mediated gene delivery in solid tumors in vivo" Cancer Letters Mar. 18, 2008; 261(2):215-225.

Kam, NWS, et al. "Carbon Nanotubes as Multifunctional Biological Transporters and Near-Infrared Agents for Selective Cancer Cell Destruction" PNAS102 (2005) 11600-11605.

Larina, IV et al. "Enhancement of Drug Delivery in Tumors by Using Interaction of Nanoparticles with Ultrasound Radiation" Technology in Cancer Research & Treatment 4(2) (2005) 217-226.

Larina, IV, Evers, BM, Esenaliev, RO, "Optimal Drug and Gene Delivery in Cancer Cells by Ultrasound-Induced Cavitation" Anticancer Research 25 (2005) 149-156.

Paliwal, S and Mitragotri, S "Ultrasound-induced Cavitation: Applications in Drug and Gene Delivery" Expert Opin. Drug Deliv. 3(6) (2006) 713-726.

Price, RJ and Kaul, S, "Contrast Ultrasound Targeted Drug and Gene Delivery: An Update on a New Therapeutic Modality" J. Cardiovasc. Pharmacol. Therapeut. 7(3) (2002) 171-180.

Seemann, S et al. "Pharmaceutical Evaluation of Gas-Filled Microparticles as Gene Delivery System" Pharmaceutical Research 19 (3) (2002) 250-257.

Sonoda S, et al. "Inhibition of Melanoma by Ultrasound-Microbubble-Aided Drug Delivery Suggests Membrane Permeabilization" Cancer Biology and Therapy 6:8 (2007) e1-e8.

Definity Prescription Insert, Lantheus Medical Imaging Oct. 2011.

Grotting JC and Beckenstein MS "Cervicofacial Rejuvenation Using Ultrasound-Assisted Lipectomy" Plastic and Reconstructive Surgery 107(3)(2001) 847-55.

Hwang JH, et al "Vascular effects induced by combined 1-MHz ultrasound and microbubble contrast agent treatment in vivo" Ultrasound in Med. & Biol. 31(4) (Apr. 2005) 553-564.

Larina IV et al. "Optimal Drug and Gene Delivery in Cancer Cells by Ultrasound-Induced Cavitation" Anticancer Research 25 (2005) 149-156.

Miller DL, et al "Diagnostic ultrasound activation of contrast agent gas bodies induces capillary rupture in mice" PNAS 97 (2000) 10179-10184.

Optison Prescription Insert, GE Healthcare, May 2008.

Pine JL, et al. "Ultrasound-Assisted Lipoplasty" Plast. Surg. Nurs. 23 (3) (2003) 101-8.

Rosenthal I, et al. "Sonodynamic therapy—a review of the synergistic effects of drugs and ultrasound" Ultrasonics Sonochemistry 11(2004) 349-63.

Santoianni P, et al "Intradermal drug delivery by low frequency sonophoresis (25KHz)" Dermatology Online Journal 10 (2)(2004) 24 (6 pages).

Schumann D, et al "Treatment of human mesenchymal stem cells with pulsed law intensity ultrasound enhances the chondrogenic phenotype in vitro" Biorheology 42 (2006) 431-443.

Sonoda et al. "Inhibition of Melanoma by Ultrasound-Microbubble-Aided Drug Delivery Suggests Membrane Permeabilization" Cancer Biology &Therapy 6:8 (2007) e1-e8.

Tezel A and Mitragotri S "Interactions of inertial cavitation bubbles with stratum corneum lipid bilayers during low-frequency sonophoresis" Biophysical Journal 85 (2003) 3502-12.

Uhlemann C., et al. "Therapeutic ultrasound in lower extremity wound management" Int. J. Low Extrem. Wounds 2 (3) (2003)152-7.

* cited by examiner ature rise per watt) over the frequency range between about 2 MHZ and about 500 MHZ for various nanoparticles.

NONINVASIVE THERAPIES IN THE ABSENCE OR PRESENCE OF EXOGENOUS PARTICULATE AGENTS

RELATED APPLICATIONS

This application claims priority to and the benefit of U.S. Provisional Patent Application Ser. No. 61/219,693, filed 23 Jun. 2009 (Jun. 23, 2009) and 61/322,515, filed 9 Apr. 2010 (Apr. 9, 2010).

BACKGROUND OF THE INVENTION

1. Field of the Invention

Embodiments of the present invention relate to methods for treating cell components, cells, organelles, organs, and/or tissues with acoustic energy, electromagnetic energy, static or alternating electric fields, and/or static or alternating magnetic fields in the presence or absence of particulate enhancing agents for therapeutic applications including enhancing drug delivery to cell components, cells, organelles, organs, and/or tissues.

More particularly, embodiments of the present invention relate to methods for treating cell components, cells, organelles, organs, and/or tissues with acoustic energy, electromagnetic energy, static and/or alternating electric fields, and/or static and/or alternating magnetic fields in the presence or absence of particulate s for therapeutic applications including enhancing drug delivery to cell components, cells, organelles, organs, and/or tissues, where the methods include determining a type of energy and/or field, which produces a desired response in a cell component, a cell type, an organelle, an organ, and/or a tissue. The methods also include irradiating with acoustic and/or electromagnetic energy and/or applying a static and/or alternating electric and/or magnetic fields to the cell component, the cell type, the organelle, the organ, and/or the tissue for a duration, at energy level and/or field level, at a frequency or frequencies sufficient to achieve a desired response in the cell component, the cell type, the organelle, the organ, and/or the tissue. The methods may also include irradiating and/or applying in the presence of particles designed to enhance therapeutic efficacy of the irradiating and/or applying.

2. Description of the Related Art

U.S. Pat. No. 6,165,440 to Esenaliev disclosed a treatment of solid tumors with acoustic and/or electromagnetic energy in the presence of nanoparticles to effectuate a therapeutic response in the tumor.

U.S. Pat. Nos. 7,144,627, 6,908,496, 6,852,252, 6,778,316, 6,699,724, 6,685,986, 6,685,730, 6,660,381, 6,645,517, 6,530,944, 6,428,811, and 6344272 disclose the use of nano-shells to enhance therapeutic treatments in a body through the placement of the nano-shells in the tissue to be treated and the particles thermalize incident radiation causing localized heating of the tissue.

Although acoustic and/or electromagnetic energy in the presence of nanoparticles have been disclosed for therapeutic applications, there is still the need in the art for new or different methods for therapeutic applications capable of being performed in the absence or presence of nanoparticles.

SUMMARY OF THE INVENTION

Embodiments of the present invention provide methods for treating cell components, cells, organelles, organs, and/or tissues with acoustic energy, electromagnetic energy, static or alternating electric fields, and/or static or alternating magnetic fields in the presence or absence of particulate enhancing agents for therapeutic applications. For treatments that are performed in the absence of particulate enhancing agents, the frequency, frequencies, frequency spectrum, and amplitude of the acoustic or electromagnetic energy along with mode of radiation—continuous, pulsed, or mixtures thereof—and the field amplitude and mode—continuous, pulsed, variable, or mixture thereof are tuned to the cell components, cells, organelles, organs, and/or tissues being treated. For treatments that are performed in the presence of particulate enhancing agents, the type of agents along with the factors controlling the energy and fields properties are tuned to the particulate enhancing agents.

Embodiments of the present invention provide methods for enhancing drug delivery including applying a pharmaceutical agent or agents to an animal including mammals and humans and applying continuous and/or non-continuous acoustic energy, continuous and/or non-continuous electromagnetic energy, static or alternating electric fields, and/or static or alternating magnetic fields to cell components, cells, organelles, organs, and/or tissues to enhance local pharmaceutical agent activity in the components, cells, organelles, organs, and/or tissues.

Embodiments of the present invention provide methods applying continuous and/or non-continuous acoustic energy, continuous and/or non-continuous electromagnetic energy, static or alternating electric fields, and/or static or alternating magnetic fields to cell components, cells, organelles, organs, and/or tissues to damage the components, cells, organelles, organs, and/or tissues and/or alter or modify the properties of the components, cells, organelles, organs, and/or tissues.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
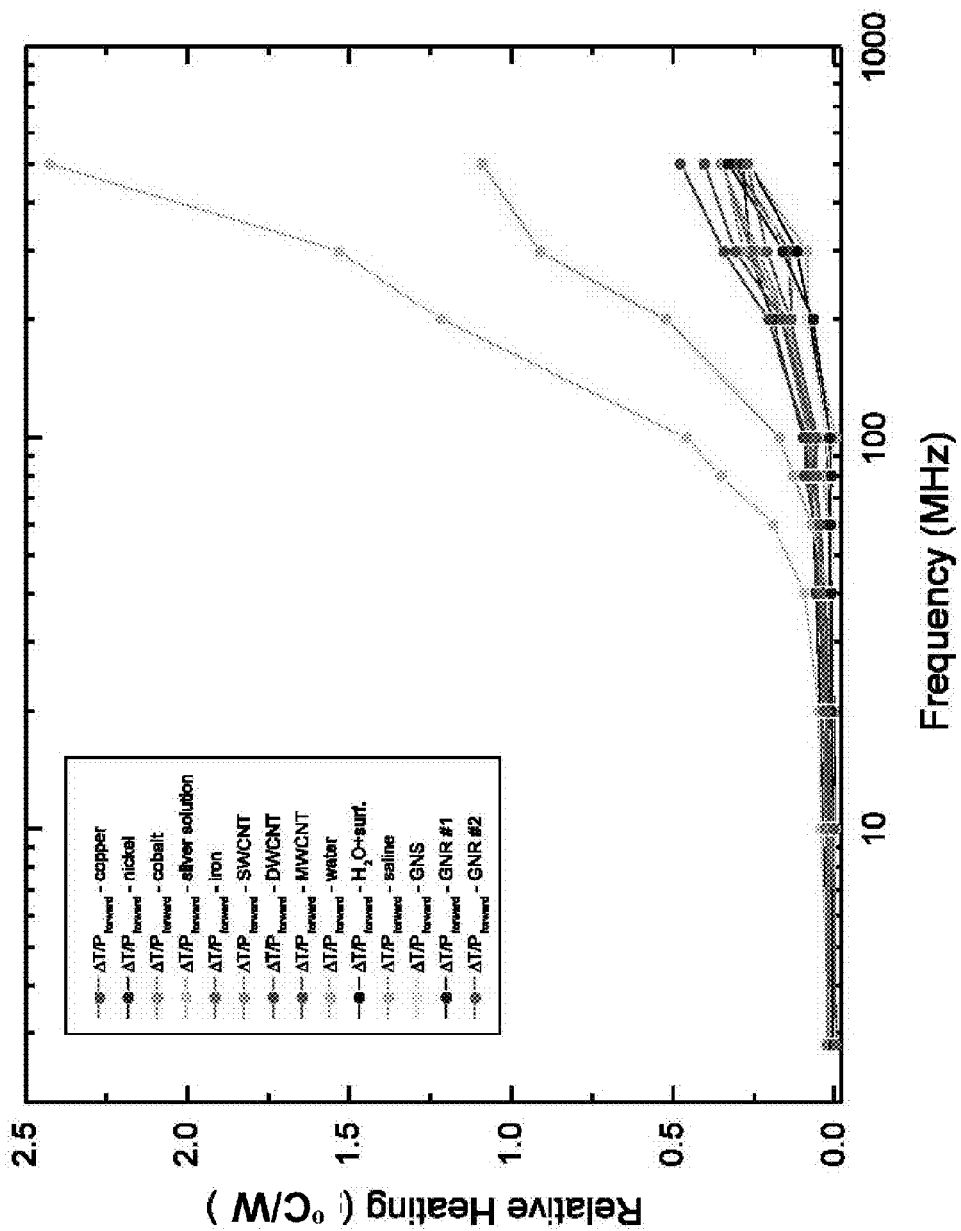
FIG. 1 depicts a plot relative heating (temperature rise per watt) over the frequency range between about 2 MHZ and about 500 MHZ for various nanoparticles.

The inventors have found that therapeutically effective treatments can be implemented, where acoustic energy, electromagnetic energy, electric fields, and/or magnetic fields in the absence or presence of particulate enhancing agents are used to induce a therapeutic response in cell components, cells, organelles, organs, and/or tissues. The therapeutic response may be to damage cell components, kill cells, and/or to augment or alter or modify cell components, cells, organelles, organs and/or tissues depending on the therapy need and intended. The energies and/or fields may also enhance drug delivery in the absence of particulate enhancing agents.

Interaction of acoustic and/or electromagnetic energy and/or electric and/or magnetic fields with cell components, cells, organelles, organs and/or tissues can result in heating, sonic vibration, cavitation, electronic excitation, and/or augmentation of other biological, chemical and/or physical properties of the cell components, cells, organelles, organs and/or tissues.

Interaction of acoustic and/or electromagnetic energy and/or electric and/or magnetic fields with pharmaceutical agent or agents being delivery to cell components, cells, organelles, organs and/or tissues can result in enhancing delivery through the heating, sonic vibration, cavitation, electronic excitation, and/or augmentation of other biological, chemical and/or physical properties of the cell components, cells, organelles, organs and/or tissues.

Interaction of radiation with particulate enhancing agents including nanoparticles and/or microparticles may be used for a variety of therapeutic applications. Radiation including, but not limited to, radio-frequency radiation, microwave, low-frequency electromagnetic wave, static electrical fields, magnetic fields, terahertz radiation, infra-red radiation, visible radiation, ultraviolet radiation, as well as ultrasound may be used in therapeutic application. In certain embodiments, a combination radiations may used for more efficient and safe therapies. In other embodiments, one frequency, a plurality of frequencies or a wide spectrum of frequencies may be used for more efficient and safe therapy. In certain embodiments, the electromagnetic waves (field) are in the frequency rage from 0 to about $3 \times 10^{19}$ Hz. In certain embodiments, the radiation is radio-frequency radiation, microwave radiation, or near infra-red range radiation to provide deep penetration in tissues and optimal interaction with nanoparticles or microparticles. In other embodiments, the radiation may be pulsed, continuous, and/or modulated. In other embodiments, the radiation is pulsed with a pulse duration having a value between about one femtosecond and one second. In other embodiments, ultrasound radiation is using having a frequency between about 20 kHz and about 1 Gigahertz.

Nanoparticles and/or microparticles suitable for use in this invention include, without limitation, metal particles, semiconductor particles, dielectric particles, metal-coated dielectric particles, metal coated semiconductor particles, polymer particles, metal coated polymer particles, bio-compatible polymer particles, bio-degradable polymer particles, or mixtures and combinations thereof. Nanoparticles and/or microparticles may be solid, liquid, gas particles, or mixtures or combinations thereof. It should be recognized that liquid nanoparticles and/or microparticles would be in the form of nano-drops or droplets and/or micro-drops or droplets. It should be recognized that gaseous nanoparticles and/or microparticles would be in the form of nano-bubbles and/or micro-bubbles. In certain embodiments, the nanoparticles may be made of gold, silver, platinum, carbon, graphite, or mixtures and combinations thereof. In other embodiments, the nanoparticles may be nano-shelled particles having a core of one material and a shell of another material. The nanoparticles include, but not limited to, spheres, rods, cylinders, disks, shells, tubes (including single-walled nanotubes), rings, irregular-shaped particles or mixtures and combinations thereof. The size of nanoparticles and microparticles may be between about 1 nanometer and about 100 microns. The nanoparticles and/or microparticles may be injected into blood, interstitially, applied topically, applied locally, subcutaneously, and/or orally depending on application and particle size, shape, and/or material. The nanoparticles and/or microparticles may be delivered using passive delivery or active delivery with targeting agents.

Therapeutic applications include, but not limited to, treatments of normal and/or abnormal tissue, stimulation and/or alteration of normal tissue, and/or cosmetic treatment. Therapy of abnormal tissues includes, but not limited to, treatments of malignant tumors or lesions, treatments of benign tumors or lesions, treatments of atherosclerotic plaques (fibrous, fatty, or calcified), treatments of blood clots, treatments of blood, treatments of amyloid plagues, treatments of neurofibrillary tangels, treatments of fibrous tissues, treatments of fatty tissue, treatments of calcified tissues, treatments of scar tissues, treatments of bone tissues, treatments of hypoxic tissues, treatments of bacteria, and/or treatments of viruses. Therapeutic applications include, but not limited to cancer therapy, atherosclerosis therapy, heart disease therapy, stroke therapy, thrombolysis, therapy of benign prostatic hyperplasia, Alzheimer's disease therapy, therapy of other neurodegenerative disorders, therapy or diabetes, and/or therapy of infections diseases. Stimulation and/or alteration of normal tissue may be used to improve and/or treat a variety of conditions and diseases including, but not limited to, stimulation and/or alteration of the immune system, stimulation and/or alteration cancer therapy, stimulation and/or alteration therapy or infectious diseases, stimulation and/or alteration ischemic tissues, and/or stimulation and/or alteration of regeneration of tissue. Cosmetic treatment includes, but not limited to, skin rejuvenation, hair removal, hair growth stimulation, fat destruction or removal.

Suitable biocompatible, biodegradable polymers include, without limitation, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof.

Typically, the polymers will either be surface erodible polymers such as polyanhydrides or bulk erodible polymers such as polyorthoesters. Poly(l-lactic acid) (PlLA), poly(dl-lactic acid) (PLA), poly(glycolic acid) (PGA), polycaprolactones, copolymers, terpolymer, higher poly-monomer polymers thereof, or combinations or mixtures thereof are preferred biocompatible, biodegradable polymers. The preferred biodegradable copolymers are lactic acid and glycolic acid copolymers sometimes referred to as poly(dl-lactic-co-glycolic acid) (PLG). The co-monomer (lactide:glycolide) ratios of the poly(DL-lactic-co-glycolic acid) are preferably between about 100:0 to about 50:50 lactic acid to glycolic acid. Most preferably, the co-monomer ratios are between about 85:15 and about 50:50 lactic acid to glycolic acid. Blends of PLA with PLG, preferably about 85:15 to about 50:50 PLG to PLA, are also used to prepare polymer materials.

PLA, PlLA, PGA, PLG and combinations or mixtures or blends thereof are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid.

Suitable polymers for use in the present invention include, without limitation, biocompatible polymers, biocompatible polymers that are biodegradable and/or bioerodible, i.e., the polymers eventually decompose in the body. The biodegradation and/or bioerodible can be by cellular degradation (e.g., macrophage degradation or the like), chemical degradation (e.g., enzymatic degradation), hydrolysis (e.g., via bodily fluids such as plasma) or other cellular action and/or the degradation or erosion can be due to degradation agents contained within the composition itself (e.g., embedded enzymes, depolymerization agents or the like). Such polymeric substances include polyesters, polyamides, polypeptides and/or polysaccharides or the like.

To enhance bio-degradation of the polymers used in biological application, the compositions of the present invention can also include the addition of enzymes that can facilitate the biodegradation of the polymers used in the composition. Preferred enzymes or similar reagents are proteases or hydrolases with ester-hydrolyzing capabilities. Such enzymes include, without limitation, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation enhancing agent can be used to regulate composition duration.

The interaction of the nanoparticles or microparticles with electromagnetic radiation can include heating of the particles and surrounding cells and tissues that, in turn, results in hyperthermia, coagulation, explosive evaporation, plasma formation, acoustic wave formation depending on the duration, frequency, energy, and/or power of electromagnetic radiation and repetition rate of electromagnetic pulses (if pulsed radiation is used). These processes result in destruction or alteration of abnormal tissue, and/or stimulation or alteration of normal tissue. The size of the thermal damage area L is dependent on thermal diffusivity $\chi \sim 1.3 \times 10^{-3}$ cm$^2$/s (of the tissue). The area L is controlled by varying a pulse duration of the radiation according to equation (1)

$$L \sim (\chi\tau)^{1/2} \qquad (1)$$

where $\tau$ is pulse duration. For instance, to induce precise damage to subcellular structures, radiation pulses may have a duration up to about 10 microsecond. To induce precise damage to individual cells, radiation pulses may have a duration of the order of 10 microsecond. To induce precise damage to millimeter-sized areas, radiation pulses may have a duration of the order of 1 second. Thus, the areas of damages are controllable by varying the pulse duration of the treating radiation.

In embodiments using acoustic radiation (e.g., ultrasound radiation,) the interactions with nanoparticles or microparticles may produce cavitation, acoustic streaming, and/or radiation force that, in turn, may result in mechanical destruction of the tissue. In certain embodiments, the precise damage to a tissue is determined by acoustic frequency, duration, energy, power, and/and pulse repetition rate.

The interaction of the nanoparticles or microparticles with radiation may be used to deliver therapeutic agents. It also may be applied in combination with other therapeutic modalities to achieve higher efficacy and safety.

The inventors have performed studies on the interaction of radiation with nanoparticles to demonstrate heating of nanoparticles by electromagnetic radiation. The inventors used electromagnetic radiation in the radio-frequency (RF) range, frequencies between about 2 MHZ and 500 MHZ. The radiation was generated by an RF generator that provided tunable, continuous wave (CW) RF radiation, which was amplified by an RF amplifier with output power of up to 50 W. A quartz cuvette with two electrodes attached to the sides was specially designed to provide irradiation of nanoparticles in water. The RF radiation was delivered to the electrodes by a high-frequency cable. The heating of the following samples was studied: water, water with surfactant, saline, gold nanoparticles (nano-spheres, nano-rods and nano-shells), silver, copper, nickel, cobalt, iron, carbon nano-tubes (single-walled, doule-walled, and multi-walled).

Figure 2:
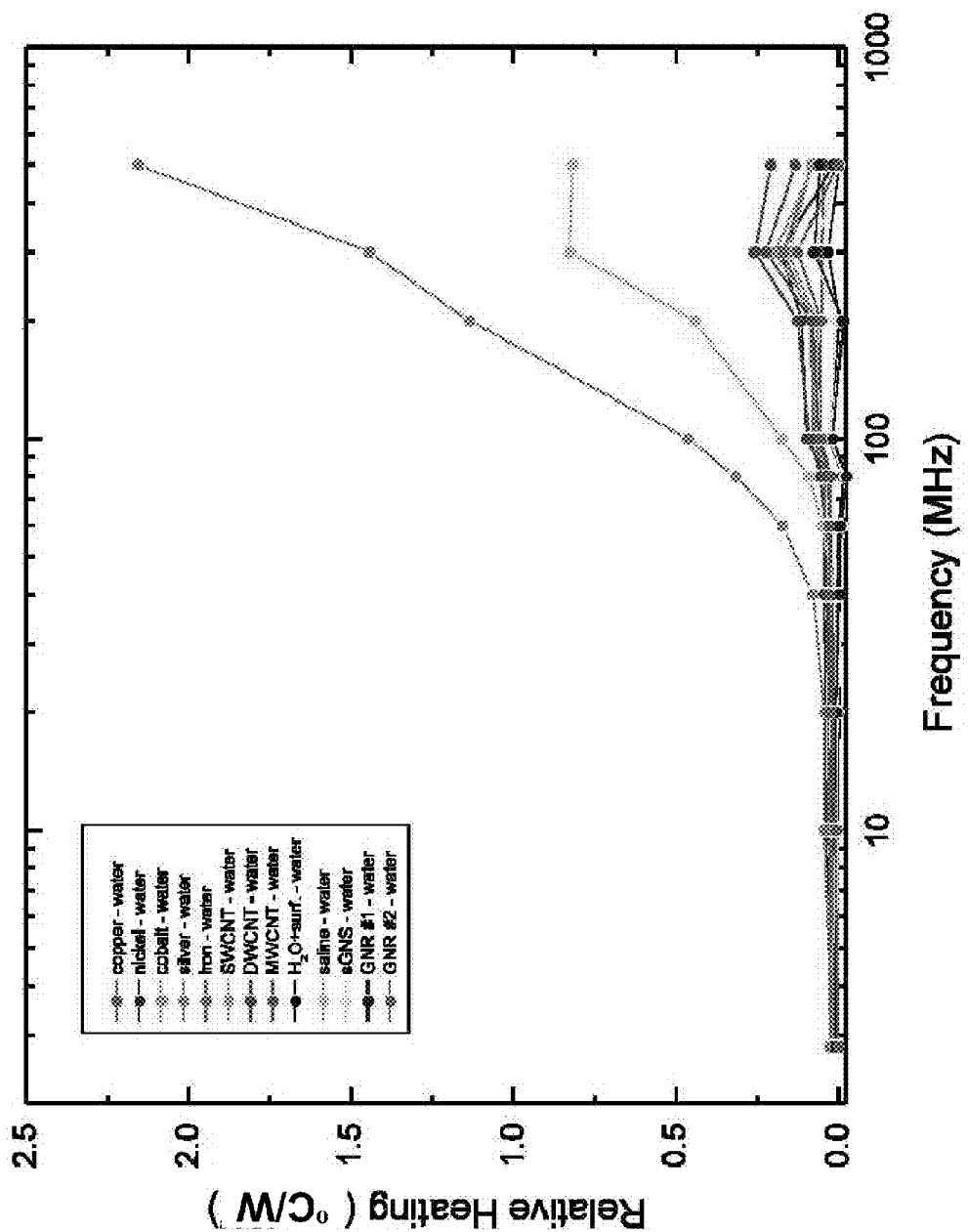
FIG. 2 depicts a plot relative heating (temperature rise per watt) over the frequency range between about 2 MHZ and about 500 MHZ for various nanoparticles.

FIG. 1 shows the relative heating (temperature rise per watt) for these samples vs. frequency. FIG. 2 shows the same data, but with water heating subtracted. Our data indicate that in certain embodiments, the frequency range between about 100 MHZ and 500 MHZ is optimal for heating the nanoparticles in an aqueous media. Moreover, all nanoparticles produce higher heating compared to that of water or water with surfactant, while silver nanoparticles produce best heating. While silver nanoparticle have low toxicity, one may coat the silver nanoparticles with gold or other non-toxic materials to further reduce toxicity.

Interaction of Radiation with Cell Components, Cells, Organelles, Organs and/or Tissues Interaction of radiation with specific tissue parts (including but limited to endogenous nano-, micro-, mm-, or cm-sized particles, layers, compartments), cells, cell organells, pathogens, or toxins can be used for a variety of therapeutic applications. Radiation includes, but not limited to, radiofrequency, microwave, low-frequency electromagnetic wave, static electrical or magnetic field, terahertz, infra-red, visible, ultraviolet, as well as ultrasound or mixtures and combinations thereof. In certain embodiments, mixtures and combinations of these radiation types may be used for more efficient and safe therapies. In other embodiments, one frequency, a plurality of frequencies, or a wide spectrum of frequencies may be used for more efficient and safe therapies. The electromagnetic waves (field) are in the frequency range between about 0 and about $3 \times 10^{19}$ Hz. In certain embodiments, the radiation is radiation in the radiofrequency, microwave, or near infra-red range to provide deep penetration in tissues and optimal interaction with tissue parts.

Radiation can be pulsed, continuous wave, or modulated. In certain embodiments, the radiation is pulsed with the pulse duration between about one femtosecond and about one second. In certain embodiments using acoustic radiation, the radiation has a frequency between about 20 kHz and about 1 Gigahertz (ultrasonic radiation). In certain embodiments, the size of tissue parts or cell organelles may be between about 1 nanometer and about 10 centimeters. Tissues include, but not limited to, normal and/or abnormal tissues. Pathogens include, but not limited to, viral pathogens, bacterial pathogens, fungal pathogens, prionic pathogens, or eucariotic pathogen organisms, or mixtures and combinations thereof.

Therapeutic applications include, but not limited, to therapy of abnormal tissue, stimulation or alteration of normal tissue, cosmetic treatment, inactivation of pathogens or toxins. Therapy of abnormal tissue includes, but not limited, to malignant tumors or lesions, benign tumors or lesions, atherosclerotic plaques (fibrous, fatty, or calcified), blood clots, blood, amyloid plagues, neurofibrillary tangels, fibrous tissues, fatty tissue, calcified tissues, scar tissues, bone tissues, hypoxic tissues, infected tissues. Therapeutic applications include, but not limited to cancer therapy, atherosclerosis therapy, heart disease therapy, stroke therapy, thrombolysis, therapy of benign prostatic hyperplasia, Alzheimer's disease therapy, therapy of other neurodegenerative disorders, therapy of diabetes, therapy of infections diseases.

Stimulation and/or alteration of normal tissue may be used to improve or treat a variety of conditions and diseases including, but not limited, to stimulation of immune system, cancer therapy, therapy or infectious diseases, ischemic tissues, regeneration of tissue. Cosmetic treatment includes, but not limited, to skin rejuvenation, hair removal, hair growth stimulation, fat destruction or removal.

The interaction of the tissue parts, cells, cell organelles, pathogens, or toxins with electromagnetic radiation can include heating of the tissue parts, cells, cell organelles, pathogens, or toxins and surrounding cells and tissues that, in turn, results in hyperthermia, coagulation, explosive evaporation, electrostriction effects, piezoelectric effects, mechanical stress, acoustic wave formation, plasma formation, depending on duration, frequency, energy, power of electromagnetic radiation and repetition rate of electromagnetic pulses. These processes result in destruction or alteration of abnormal tissue, stimulation or alteration of normal tissue. As stated previously, the size of the thermal damage area L depends on thermal diffusivity $\chi \sim 1.3 \times 10^{-3}$ cm$^2$/s of the tissue and is controllable by varying the pulse duration according to Equation (1):

$$L \sim (\chi \tau)^{1/2} \quad (1)$$

where $\tau$ is the pulse duration. For instance, to induce precise damage to subcellular structures one can use short pulses with duration up to about 10 microsecond, to induce precise damage to individual cells one can use pulses with duration of the order of 10 microsecond, to induce precise damage to millimeter-sized areas one can use pulses with duration of the order of 1 second, etc.

Interaction of ultrasound with the tissue parts, cells, cell organelles, pathogens, or toxins may produce cavitation, acoustic streaming, and radiation force that, in turn, result in mechanical destruction of the tissue parts, cells, cell organells, pathogens, or toxins. One can produce precise damage to tissues by varying ultrasound frequency, duration, energy, power, and pulse repetition rate.

Selective damage to the tissue parts, cells, cell organells, pathogens, or toxins may be produced by the radiation when contrast in electromagnetic (radiofrequency, microwave, low-frequency electromagnetic wave, static electrical or magnetic field, terahertz, infra-red, visible, ultraviolet) or acoustic properties of the tissue parts, cells, cell organels, pathogens, or toxins is substantial.

Optimization of radiation parameters (duration, frequency, energy, power of electromagnetic radiation and repetition rate of electromagnetic pulses and ultrasound frequency, duration, energy, power, and pulse repetition rate) may be used to improve selective damage to the tissue parts, cells, cell organells, pathogens, or toxins and to improve therapeutic outcome.

The interaction of radiation with the tissue parts, cells, cell organelles, pathogens, or toxins may be used for delivery of therapeutic agents. The radiation may also be applied in combination with other therapeutic modalities for higher efficacy and safety. This noninvasive therapy may also be used for therapy of human patients as well as animals including companion animals.

One can use exogenous dyes, electromagnetic radiation active, or ultrasound radiation active substances to enhance therapeutic effects. Nanoparticles and microparticles may be used to enhance the therapeutic effect of radiation as described above.

Proteins, lipids, nucleic acids, carbohydrates, water and other molecules, organelles, tissue parts, pathogens have higher absorption at some wavelengths and frequencies compared to the other constituents. This allows for selective damage to these molecules, organelles, tissue parts, in particular, if pulsed radiation is used. For instance: 1) higher absorption by cancer cell nucleus results in selective damage to cancer cells that may be used for cancer therapy; 2) higher absorption by peptidoglycan and/or lipids results in selective damage to bacterial membrane that may be used for therapy of infectious diseases and inactivation of bacteria in the body or in surrounding environment including, but limited to, water, food, drugs, or during organ or tissue transplantations; 3) higher absorption by nucleic acids or proteins results in selective damage to viral pathogens that may be used for therapy of infectious diseases and inactivation of bacteria in the body or in surrounding environment including, but limited to, water, food, drugs, or during organ or tissue transplantations; 4) higher absorption by proteins results in selective damage to amyloid plaques that may be used for therapy of neurodegenerative disorders. Moreover, one may use difference in size between normal and abnormal cells or cell organelles for selective damage to abnormal cells, organelles, and tissues to provide better therapeutic outcome. For instance, cancer cell nucleus is typically larger than that of normal cell. This can be used for safe and efficient cancer therapy because heat diffusion from cancer cell nucleus is slower than from the nucleus of the normal cell.

These examples are given for the purpose of demonstration of potential therapies, but not for limitations of this technology.

The present technology may be used in combination with other therapeutic modalities including, but not limited, to drug therapy (such as chemotherapy), biotherapy, surgery, conventional radiation therapy, physiotherapy. In certain embodiments, wearable acoustic or electromagnetic devices or transducers of acoustic or electromagnetic energy are used to provide long duration of treatment. The acoustic or electromagnetic energy may be used to provide treatment in a hospital, inpatient, outpatient, home environment or during everyday normal activity for more efficient therapy.

The present technology may be used in combination with imaging technologies and procedures to improve therapy or imaging outcome.

These forms of radiation may be delivered using optical fibers, electromagnetic antennas, acoustic transducers in non-contact or contact mode by attaching them to the skin surface, transcutaneously, interstitially, endoscopically, or by using whole body irradiation.

Ultrasonic Treatments to Enhance Drug Delivery
Biodegradable PLGA Nanoparticles

The PLGA nanoparticles have the following advantages: they are biodegradable, they can be delivered in tumor blood vessels at higher concentrations compared to microparticles or gas micro-bubbles due to the EPR effect, they provide cavitation for longer time, and they provide cavitation at low ultrasound pressure. PLGA is a biodegradable polymer which is being used in patients as a material for surgical sutures. Our laboratory manufactures them with double (water/oil)/water (W/O)/W emulsion solvent evaporation technique using biodegradable polymer Poly(D,L-lactide-co-glycolic acid 50:50, PLGA).

Figure 3A:
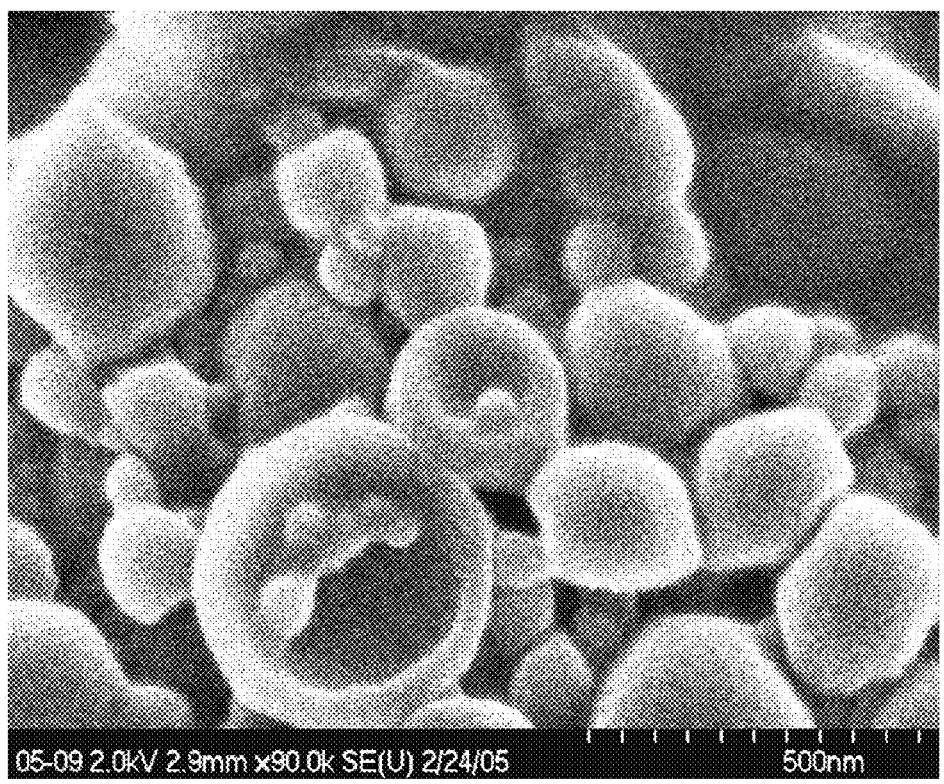
FIG. 3A depicts scanning Electron Microscopy of PLGA nanoparticles.
Figure 3B:
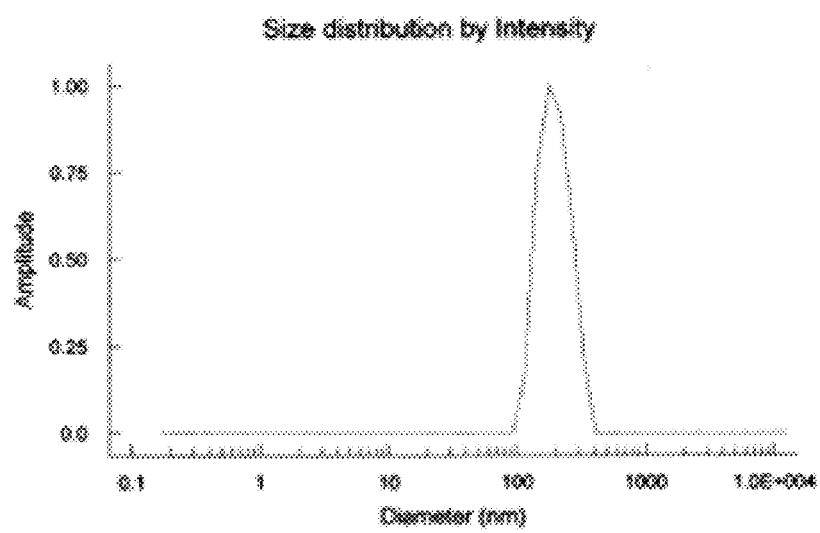
FIG. 3B depicts typical size distributions of filtered PLGA nanoparticles (1 mg/mL in water).

We used microscopy techniques (SEM and optical) as well as particle sizers to evaluate PLGA particle size and structure. FIG. 3A shows a SEM picture of PLGA nanoparticles. FIG. 3B shows a typical particle size distribution of filtered PLGA nanoparticles (about 200 nm) used in the studies.

Figure 4:
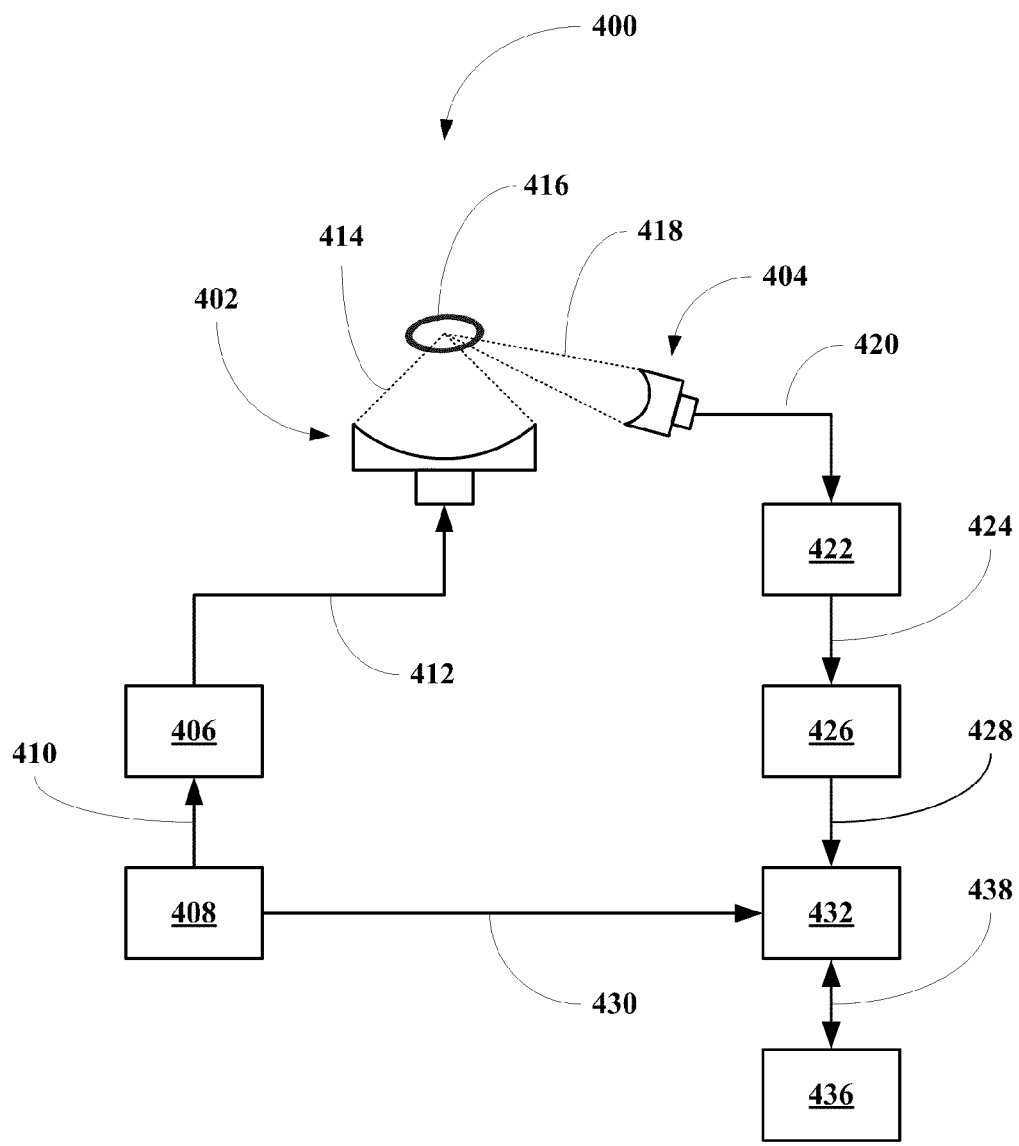
FIG. 4 depicts an experimental setup for ultrasound irradiation of tumors in mice and detection of cavitation.

Referring to FIG. 4, an embodiment of an ultrasound system of this invention, generally 400, is shown to include an irradiation focusing transducer 402 and a receiving focusing transducer 404. The irradiation focusing transducer 402 connected to a power amplifier 406, which is connected to a signal generator 408. The irradiation focusing transducer 402 has a resonance frequency of 1 MHZ and the receiving focusing transducer 404 has a resonance frequency of 5 MHZ, which is adapted to detect cavitation signals and activity at 5 MHZ. The signal generator 408 is a pulse/function generator (8116A, Hewlett-Packard) and generates a ultrasound signal 410. The power amplifier 406 is an Rf Power amplifier (2100L ENI) and amplifies the ultrasonic signal 410 to produce an amplified ultrasonic signal 412. The generator 408 and the amplifier 406 were used for generation and amplification of electrical signals for the irradiating the irradiation transducer 402. The system 400 allows measuring cavitation signals with minimal noise associated with other non-linear acoustic effects. In certain embodiments, the system 400 irradiates with short ultrasound pulses having a duration between about 100 ns to about 1 ms with a repetition rate between about 1 Hz to about 1 KHz to induce cavitation. In other embodiments, the system 400 irradiates with short ultrasound pulses having a duration of about 30 μs with a repetition rate of about 20 Hz to induce cavitation. The irradiation focusing transducer 402 is positioned to focus ultrasonic radiation 414 on a tumor 416, with the receiving focusing transducer 404 positioned to receive an output signal 418 from the irradiated tumor 416. The transducer 404 converts the output signal 418 into an electronic signal 420. The signal 420 from the transducer 404 is passed through a high pass filter 422 resulting in a filter signal 424, which is then forwarded to a signal amplifier 426 resulting in an amplified, filter signal 428. The amplified signal 428 from the signal amplifier 426 and an output 430 from the signal generator 408 are passed through an ADC board 432 to form a ADC output signal 434. The output signal 428 of the ADC board 426 is forwarded to a computer 436 via a bi-directional communication GPIB cable 438.

Figure 5A:
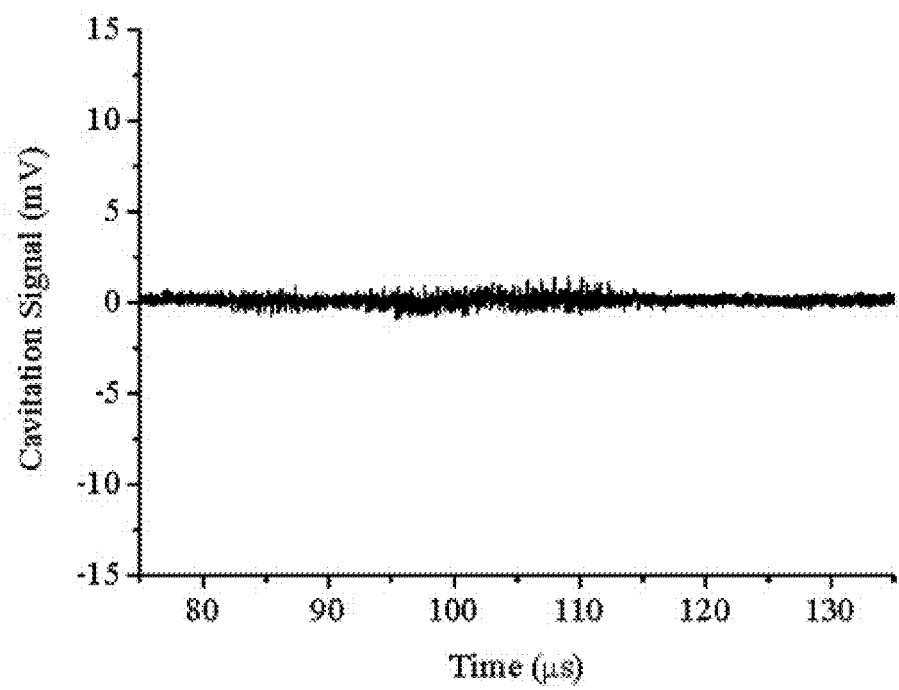
FIG. 5A a typical cavitation signal obtained from pure water.
Figure 5B:
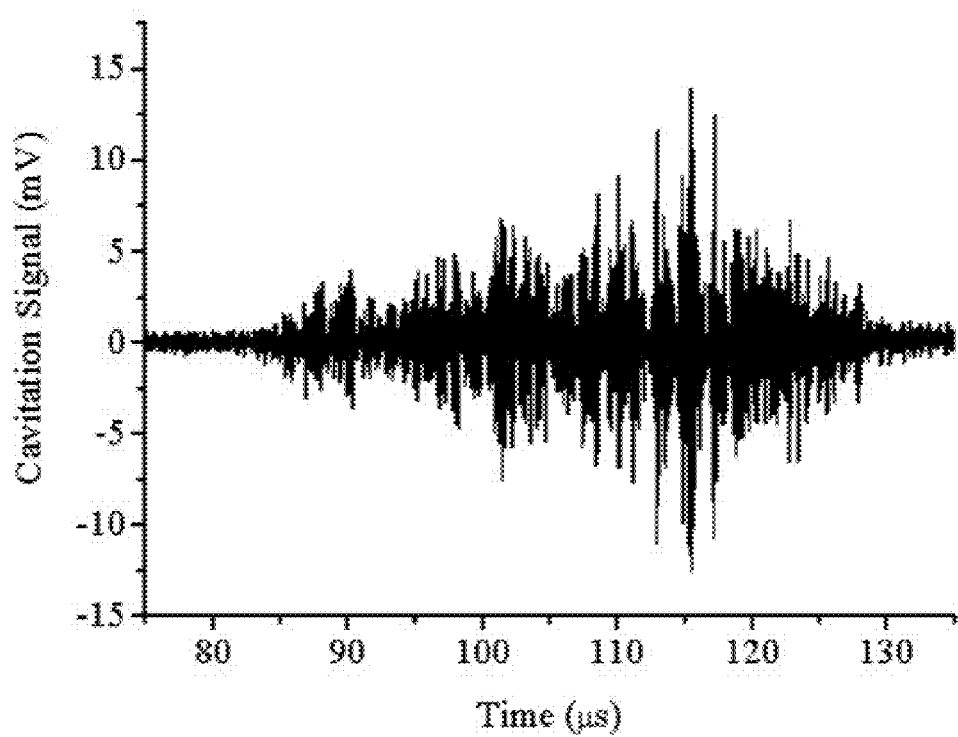
FIG. 5B a typical cavitation signal obtained from water with PLGA nanoparticles.
Figure 6A:
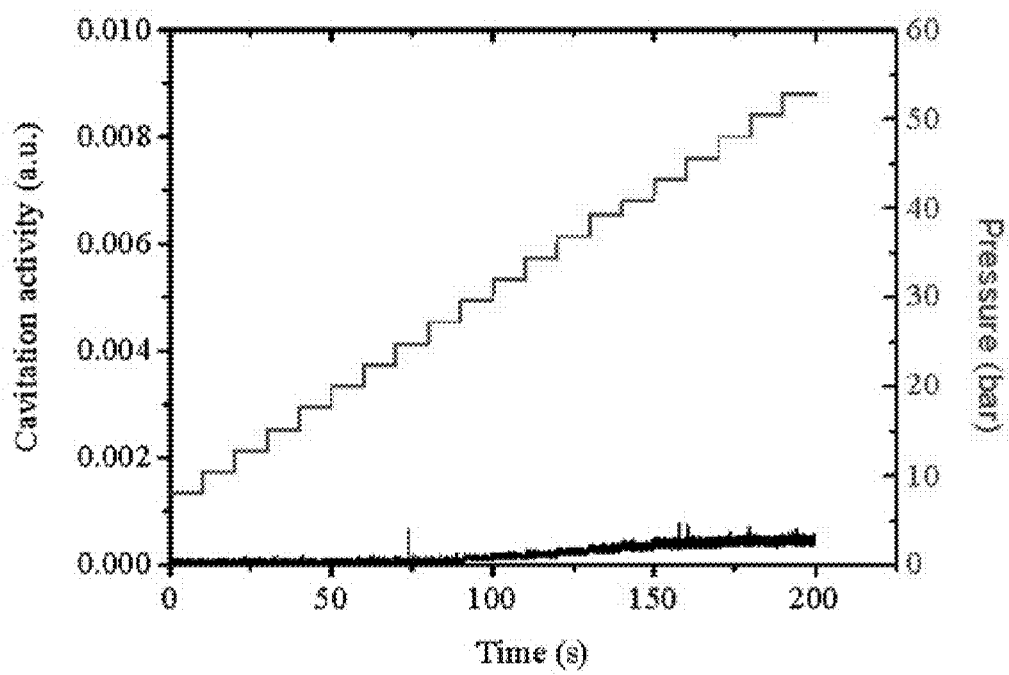
FIG. 6A a cavitation activity measured in pure water at different ultrasound pressure.
Figure 6B:
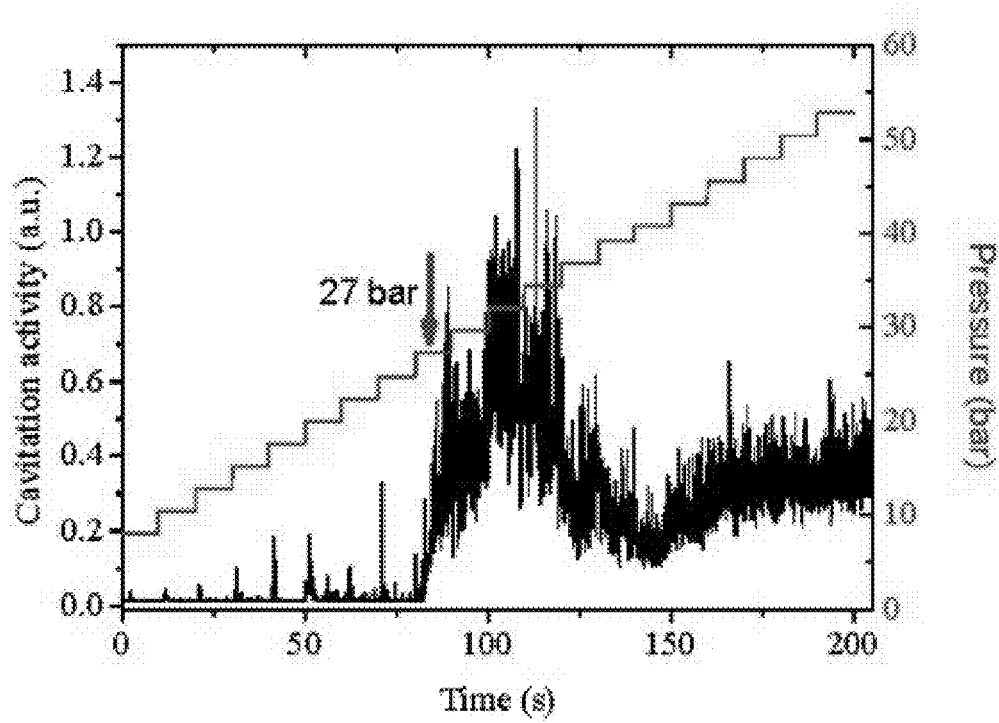
FIG. 6B a cavitation activity measured in water with PLGA nanoparticles at different ultrasound pressure.

We studied cavitation threshold and activity in pure water and in water with PLGA nanoparticles as well as in vivo in nude mice with tumors. FIG. 5A and FIG. 5B show cavitation signals obtained at same ultrasound pressure from pure water and from water with PLGA nanoparticles, respectively. The cavitation signal obtained from water with PLGA nanoparticles was significantly greater. We integrated the signals by using a procedure described in detail in I. V., Evers B. M., Ashitkov T. V., Bartels C., Larin K. V., Esenaliev R. O. Enhancement of Drug Delivery in Tumors by Using Interaction of Nanoparticles with Ultrasound Radiation. Technology in Cancer Research and Treatment, v. 4(2), 2005, pp. 217-226.

measure cavitation activity at different pressure (cavitation activity is proportional to concentration of cavitation bubbles and strength of individual cavitation events). FIG. 6A and FIG. 6B show cavitation activity measured in pure water and in water with PLGA nanoparticles, respectively. Ultrasound pressure (right Y-axis) was increased step by step during the measurements. The cavitation activity was substantially greater in water with PLGA nanoparticles than that measured in pure water. These experiments allowed to measure cavitation threshold (sharp increase of cavitation activity) which was 27 bar for water with PLGA nanoparticles at these experimental conditions. No sharp increase of cavitation activity was detected in pure water because cavitation threshold was very high.

Figure 7A:
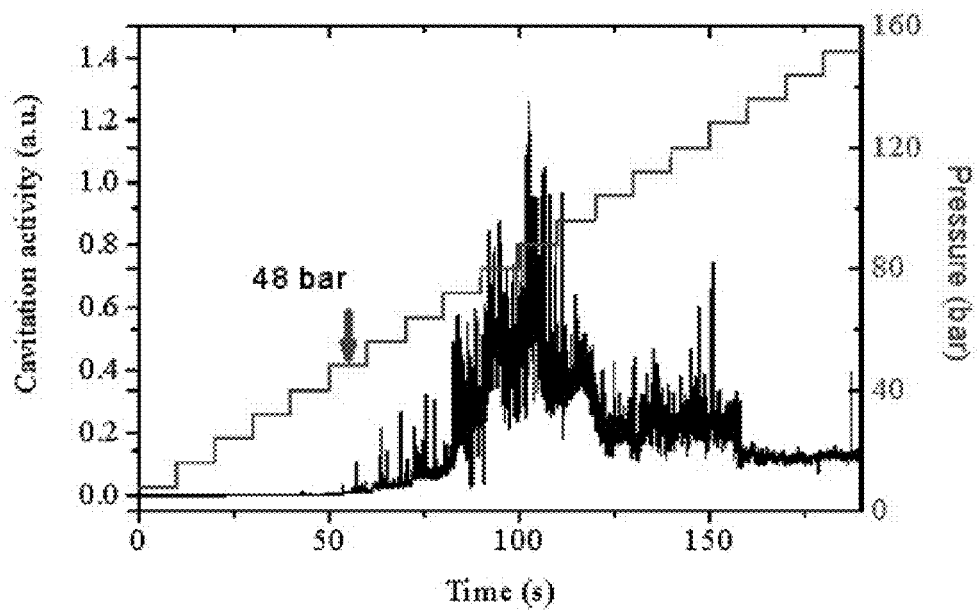
FIG. 7A a cavitation activity measured in vivo in KM20 tumor of a nude mouse after injection of Optison.
Figure 7B:
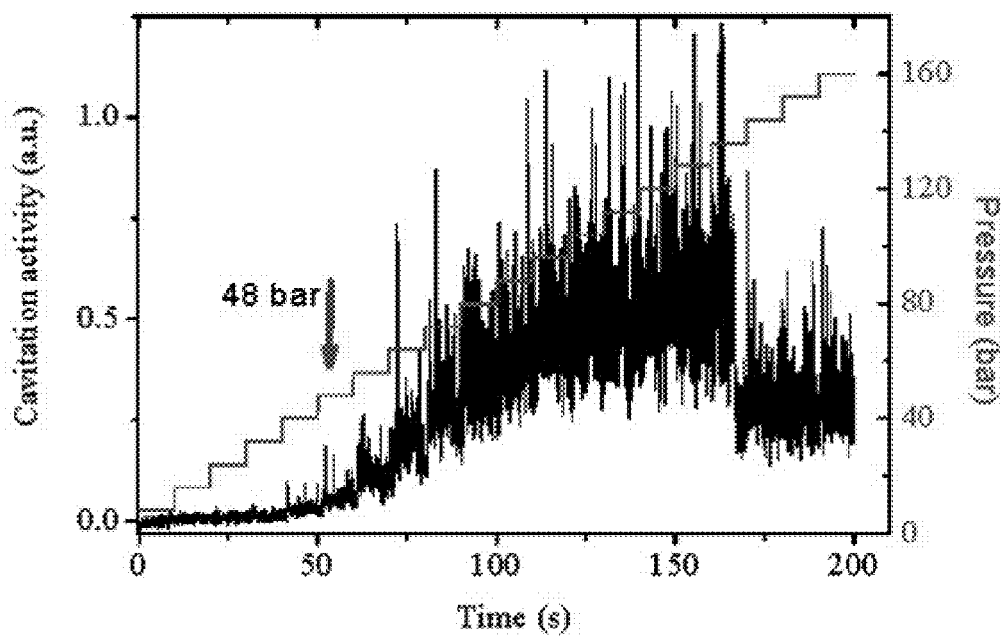
FIG. 7B a cavitation activity measured in vivo in KM20 tumor of a nude mouse after injection of PLGA nanoparticles.

Our in vivo experiments were performed with mice bearing KM20 tumors. We injected Optison or PLGA nanoparticles in the tail vein and measured cavitation signals and activity using same approach as in the experiments with water. FIG. 7A shows cavitation activity measured from a tumor of a mouse injected with Optison prior to irradiation. We detected cavitation activity with the threshold of about 48 bar. However, the cavitation activity decreased rapidly due to degradation of Optison upon ultrasound irradiation. Injection of another mouse with PLGA nanoparticles (24 hours prior to irradiation to allow for accumulation of the nanoparticles in tumors) also induced cavitation activity in the irradiated tumor (with almost same threshold) as shown in FIG. 7B. However, PLGA nanoparticles produce stable cavitation for a longer time because they degrade at a much slower rate. These studies demonstrate that PLGA nanoparticles: (1) substantially lower cavitation threshold; (2) produce cavitation in vivo; and (3) produce more stable cavitation in vivo compared with that obtained with Optison.

Model Macromolecular Drug

Figure 8A:
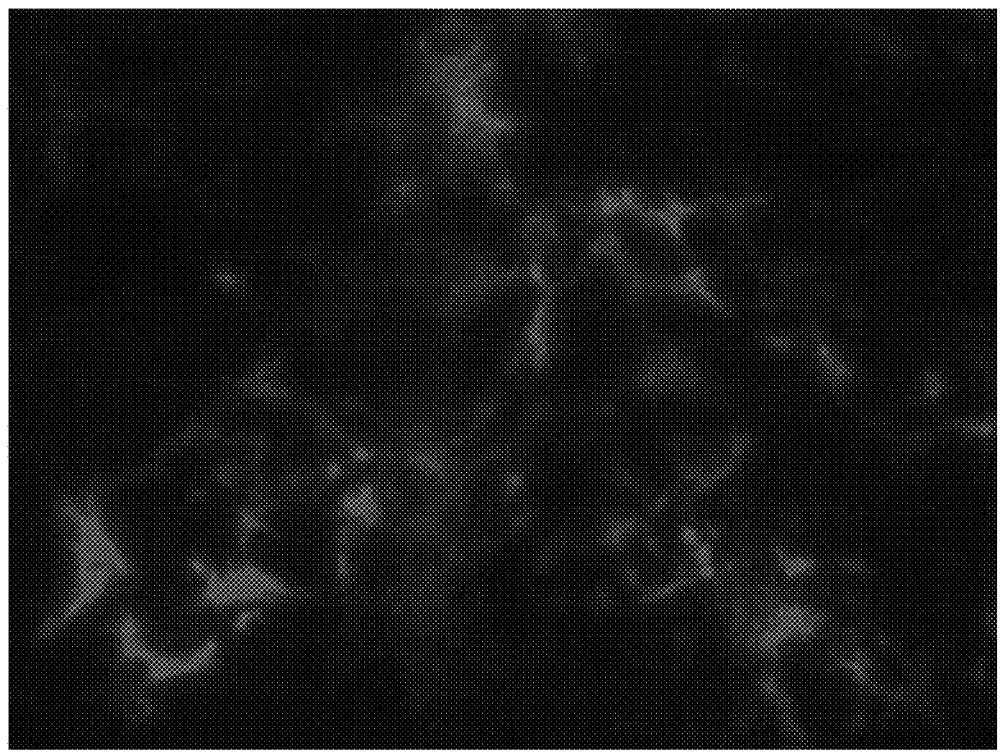
FIG. 8A a fluorescence microscopy of tumor irradiated with 1 MHZ ultrasound.
Figure 8B:
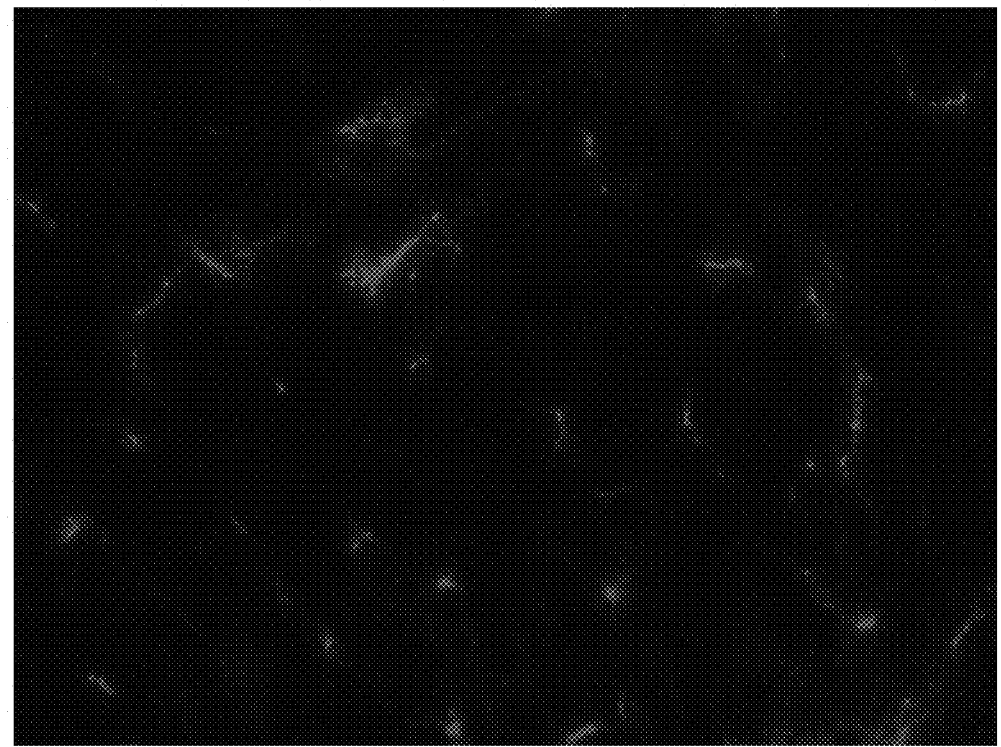
FIG. 8B a fluorescence microscopy of non-irradiated tumor.

Rhodamine-dextran (MW=2,000 kDa) (Sigma, Co.) was used as a model drug with high molecular weight. It was injected in the tail vein prior to irradiation (0.1 mL, 1% solution in saline). Tumor blood vessels were stained by using CD-31. We performed a pilot study with 1-MHZ ultrasound in vivo and the rhodamine-dextran and Optison. FIG. 8A shows much deeper penetration of rhodamine-dextran in KM20 tumor irradiated by 1-MHZ ultrasound compared to non-irradiated tumor as shown in FIG. 8B.

Figure 9A:
FIG. 9A a tumor image obtained with the high-resolution ultrasound system.
Figure 9B:
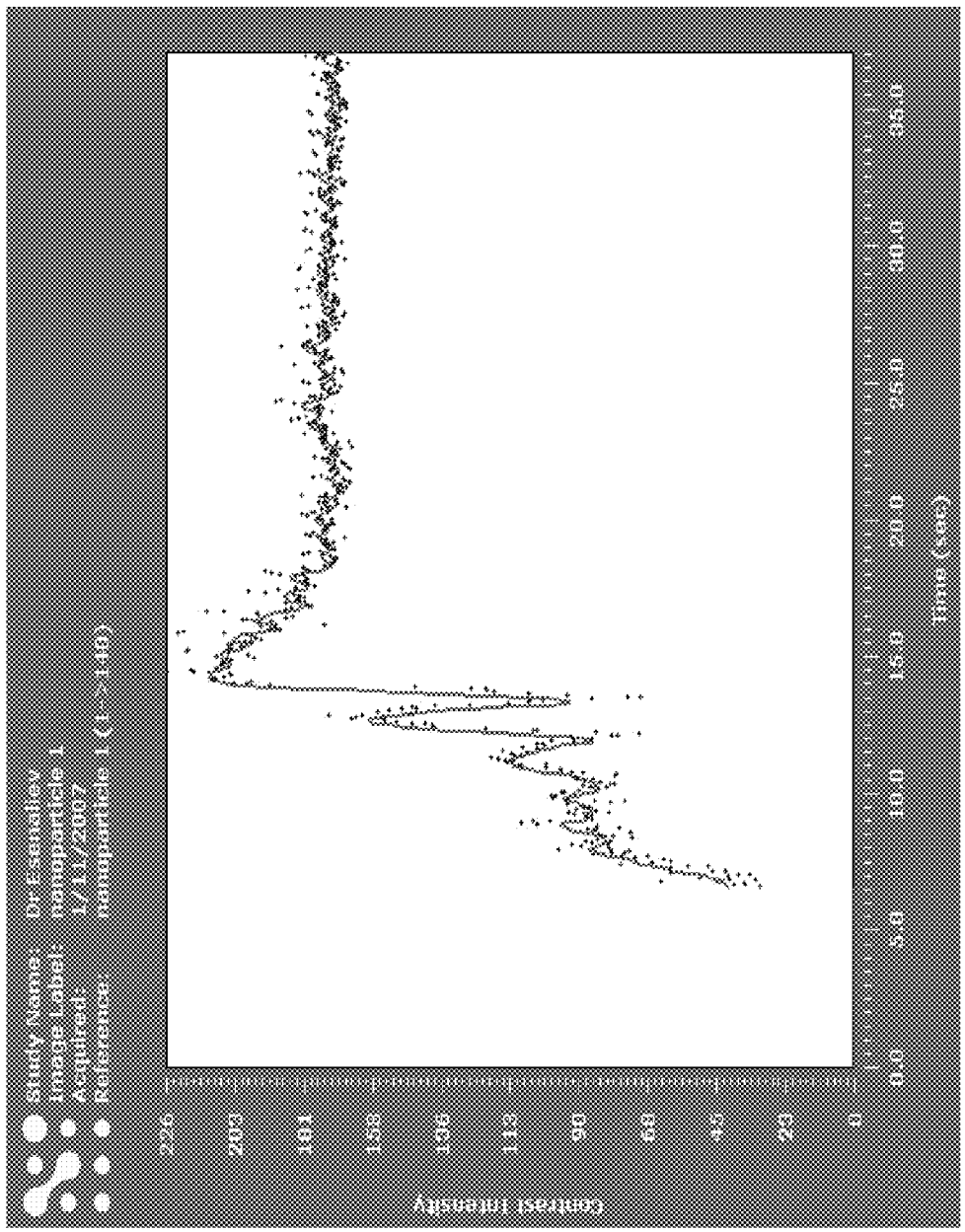
FIG. 9B a kinetics of the PLGA nanoparticles in the tumor shown in FIG. 9A.

We also monitored kinetics of the PLGA nanoparticles in tumors by using a high-resolution ultrasound imaging system. The system has the ability to visualize and quantify tumors, hemodynamics, and therapeutic interventions with resolution down to 30 microns noninvasively and in real time. FIG. 9A shows an image of a DU 145 prostate tumor in a nude mouse obtained with the system. Injection of the PLGA nanoparticles in the mouse demonstrated almost constant concentration of the PLGA nanoparticles 15 seconds after the injection as shown in FIG. 9B. This effect resulted from competition of two processes: 1) the decrease of nanoparticle concentration in blood and 2) the increase of their concentration in the tumor blood vessels due to the EPR effect. These data indicate that the system is capable of detecting the nanoparticles in tumors in vivo and that these nanoparticles are have very strong interaction with ultrasound and can be used for efficient drug delivery.

Noninvasive Therapy Applications

All these methods and systems may be used without limitations in humans (both in patients and in healthy individuals) and in any animals including mammals and companion animals (such as dogs, cats, etc.).

All these methods and systems may be used without limitations in tissues and body fluids (blood, etc.), outside of animal bodies including mammal bodies and human bodies. These methods and systems may be used for therapy of abnormal tissues or stimulation of normal tissue during tissue or organ transplantation, blood transfusion, hemodialysis, bypass surgery, and other therapies of tissues and body fluids outside of animal bodies including mammal bodies and human bodies.

Therapies with Nanoparticles and Radiation

Figure 10A:
FIG. 10A depicts a metastatic cancer in liver (the multiple tumors) obtained with high-resolution ultrasound imaging system.
Figure 10B:
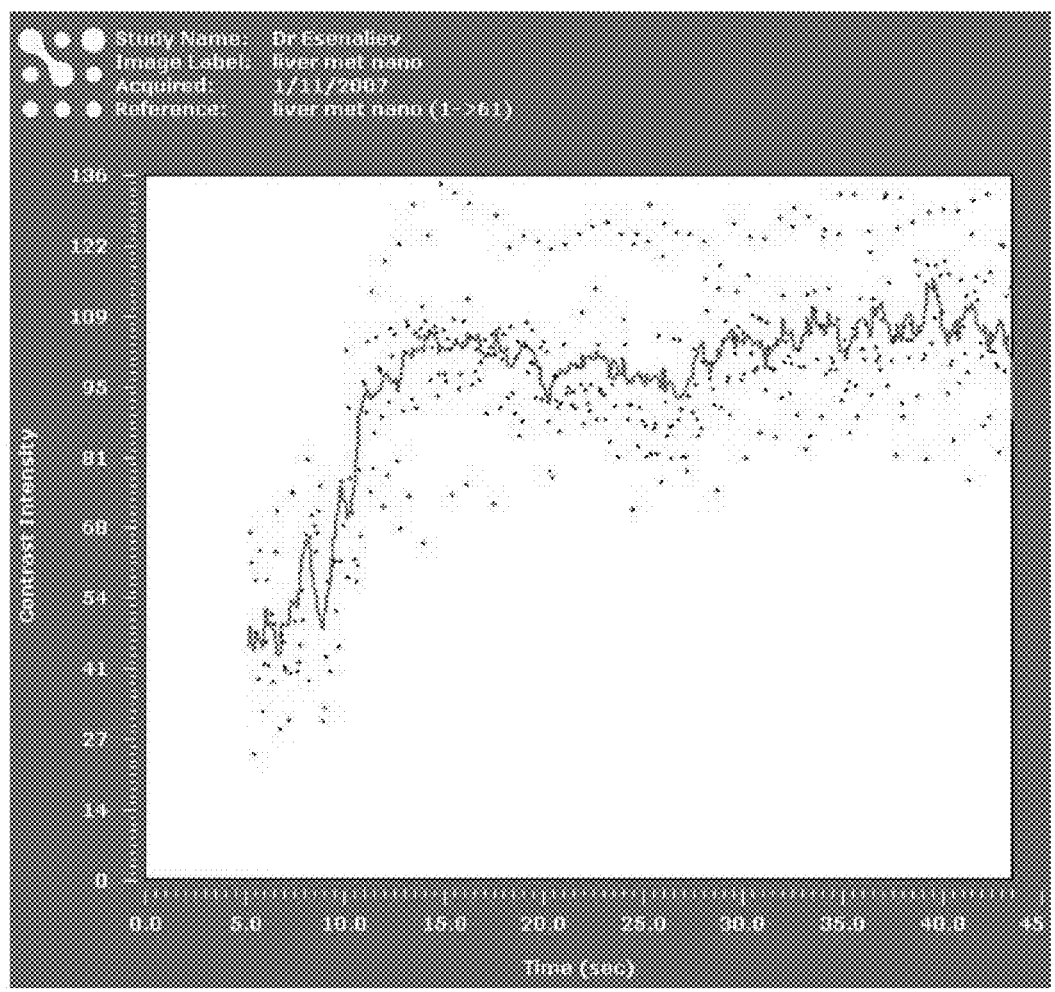
FIG. 10B depicts a penetration of the specially developed biodegradable PLGA nanoparticles in the specific tumor marked in FIG. 10A.

We developed biodegradable PLGA nanoparticles for drug delivery in abnormal tissues and for therapy without drugs. FIG. 10A shows metastatic cancer in liver (the multiple tumors) obtained with a high-resolution ultrasound imaging system. FIG. 10B shows penetration of biodegradable PLGA nanoparticles in the specific tumor marked in FIG. 10A. These data demonstrate that these methods and systems may be used for PLGA nanoparticle-based therapy of metastatic tumors (and other abnormal lesions) in liver and other organs.

Figure 11A:
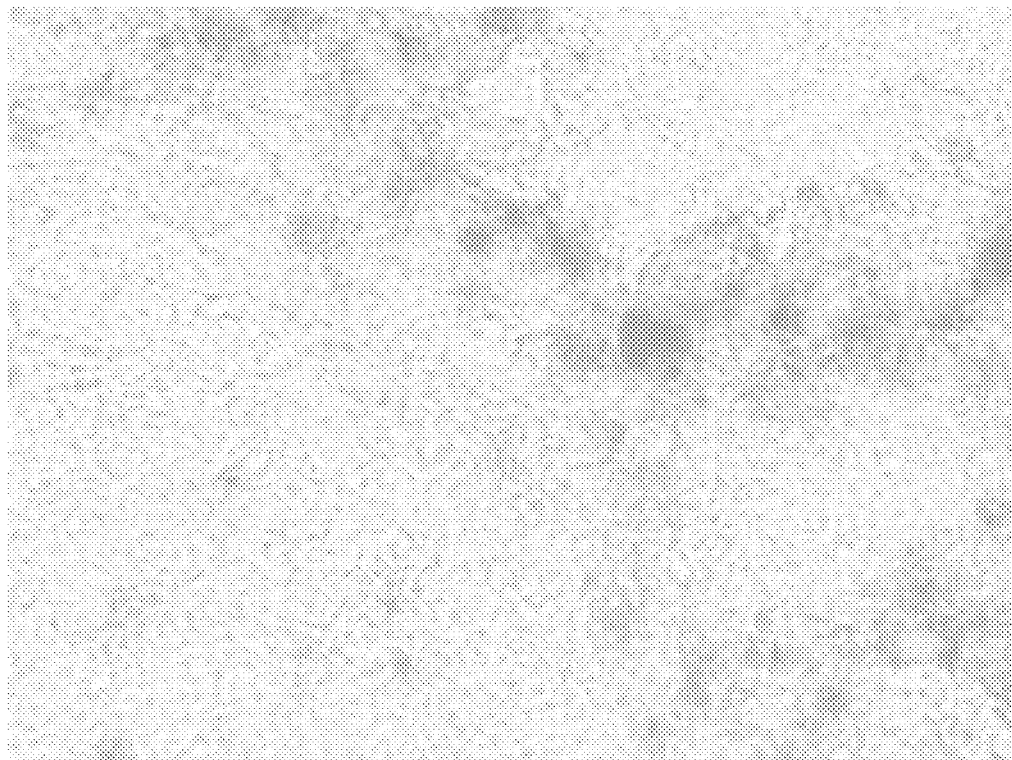
FIG. 11A depicts a gene delivery and cell transfection in vivo obtained using interaction of PLGA nanoparticles with pulsed ultrasound.
Figure 11B:
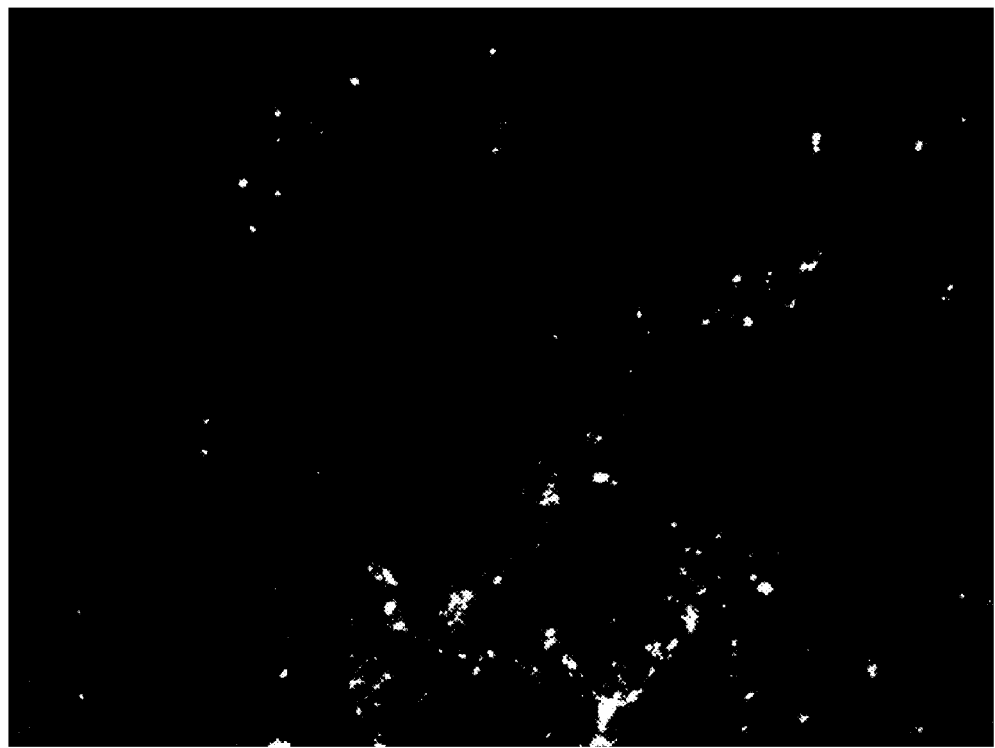
FIG. 11B depicts a penetration of the biodegradable PLGA nanoparticles in the abnormal tissue after ultrasound irradiation.

We also developed a method to load drugs and genes in the PLGA nanoparticles. FIG. 11A shows gene delivery and cell transfection in vivo obtained using interaction of the PLGA nanoparticles (loaded with beta-gal) with pulsed ultrasound. FIG. 11B shows penetration of the biodegradable PLGA nanoparticles in the abnormal tissue after ultrasound irradiation.

Figure 12A:
FIG. 12A depicts a multiple lesions induced in abnormal tissue using interaction of PLGA nanoparticles with pulsed ultrasound.
Figure 12B:
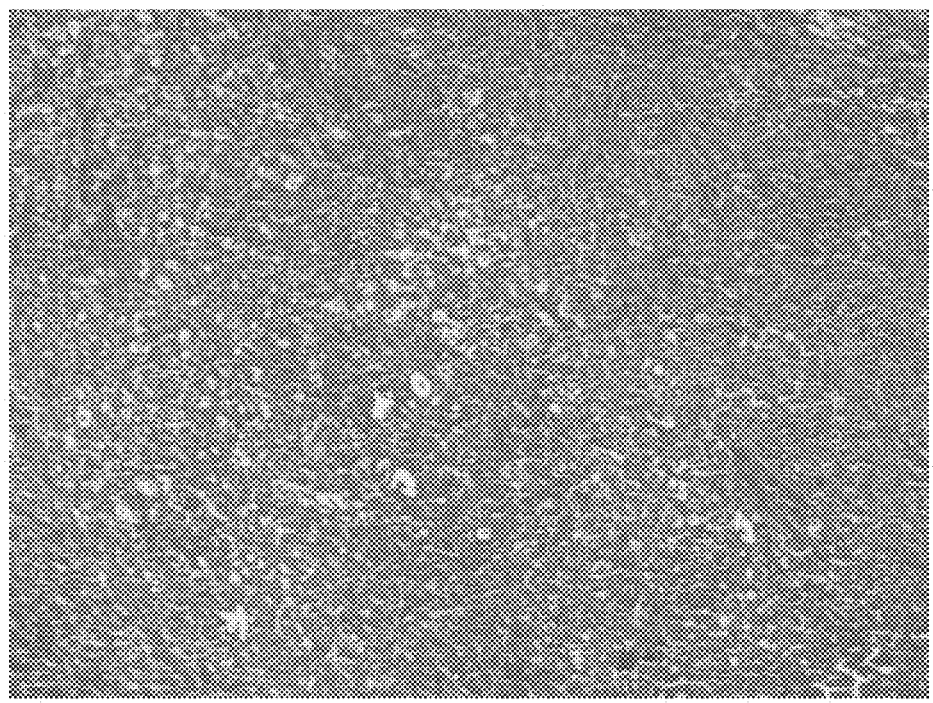
FIG. 12B shows no damage is induced by the PLGA nanoparticles in non-irradiated (control) part of the abnormal tissue.

FIG. 12A shows multiple lesions induced in abnormal tissue using interaction of the PLGA nanoparticles with pulsed ultrasound. FIG. 12B shows no damage is induced by the PLGA nanoparticles in non-irradiated (control) part of the abnormal tissue.

FIG. 13A-D shows different extent and severity of damage (microbubbles) in abnormal tissue phantom induced by pulsed electromagnetic heating of absorbing carbon nanoparticles. The fluence of the near infra-red laser pulses was 0.35 J/cm$^2$, 0.7 J/cm$^2$, 1.05 J/cm$^2$, and 1.4 J/cm$^2$ for FIG. 13A, FIG. 13B, FIG. 13C, and FIG. 13D, respectively. Each sample was irradiated with 100 pulses.

Figure 14A:
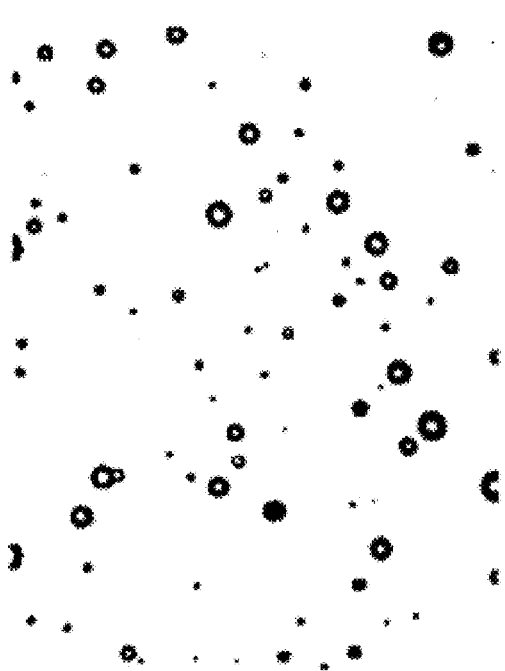
FIGS. 14A&B depict different extent and severity of damage induced by pulsed electromagnetic heating of absorbing nanoparticles.

FIGS. 14A&B shows different extent and severity of damage (microbubbles) in abnormal tissue phantom induced by pulsed electromagnetic heating of absorbing carbon nanoparticles. One pulse was used for the sample in FIG. 14A and 10 pulses were used for the sample in FIG. 14B. The fluence of the near infra-red laser pulses was 1.05 J/cm$^2$ for both samples.

Figure 13A:
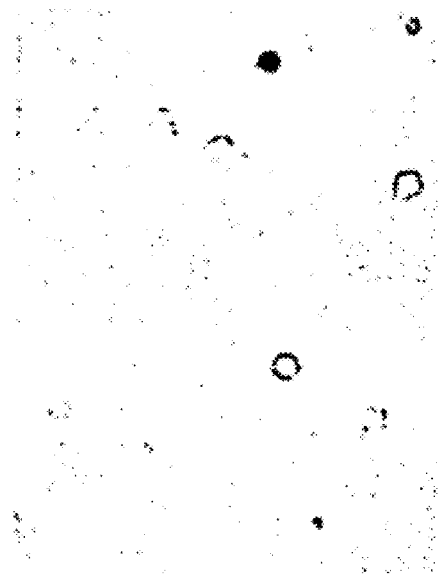
FIGS. 13A-D depict different extent and severity of damage induced by pulsed electromagnetic heating of absorbing nanoparticles.
Figure 13B:
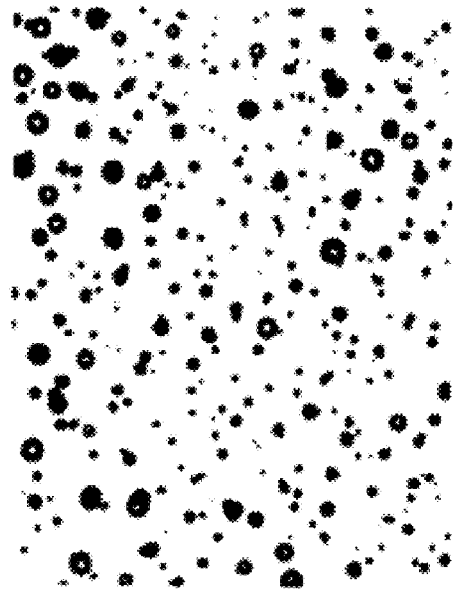
Figure 13C:
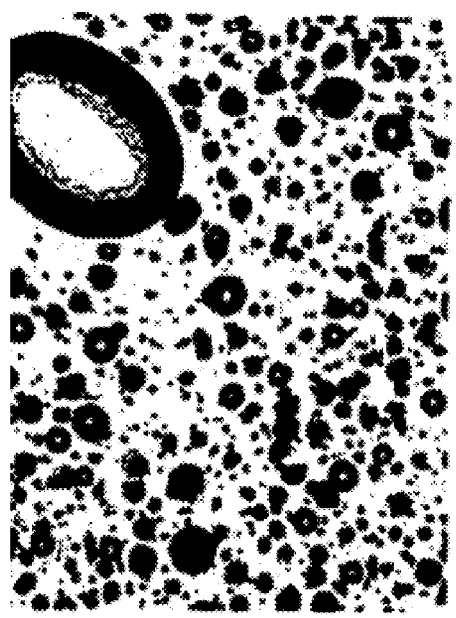
Figure 13D:
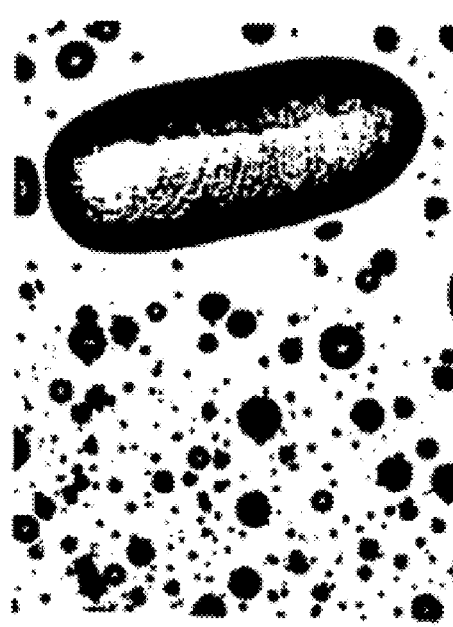
Figure 14B:
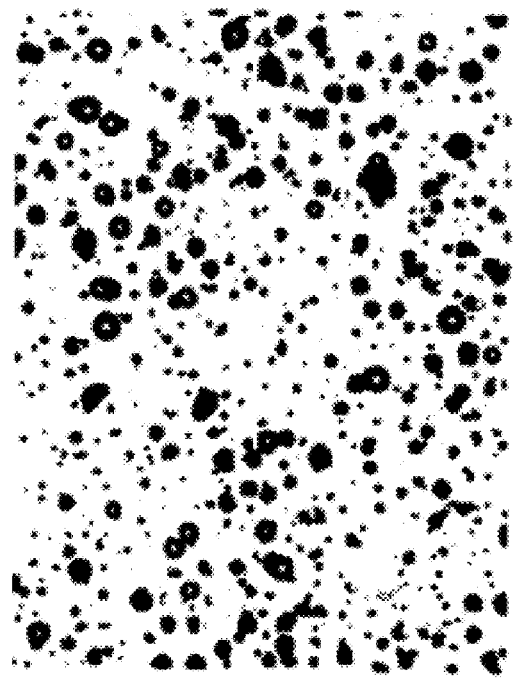

The data in FIGS. 13A-D and FIGS. 14A&B demonstrate that, by varying the parameters of electromagnetic radiation, one can control the extent and severity of the damage to abnormal tissue and limit the damage to surrounding normal tissue. For instance, uniform and precise damage may be induced in the abnormal tissue, without damage to normal tissue, when optimal parameters of radiation are used as shown in FIG. 13B and FIG. 14B.

Therapies without Nanoparticles (Therapy with Radiation Only)

Figure 15A:
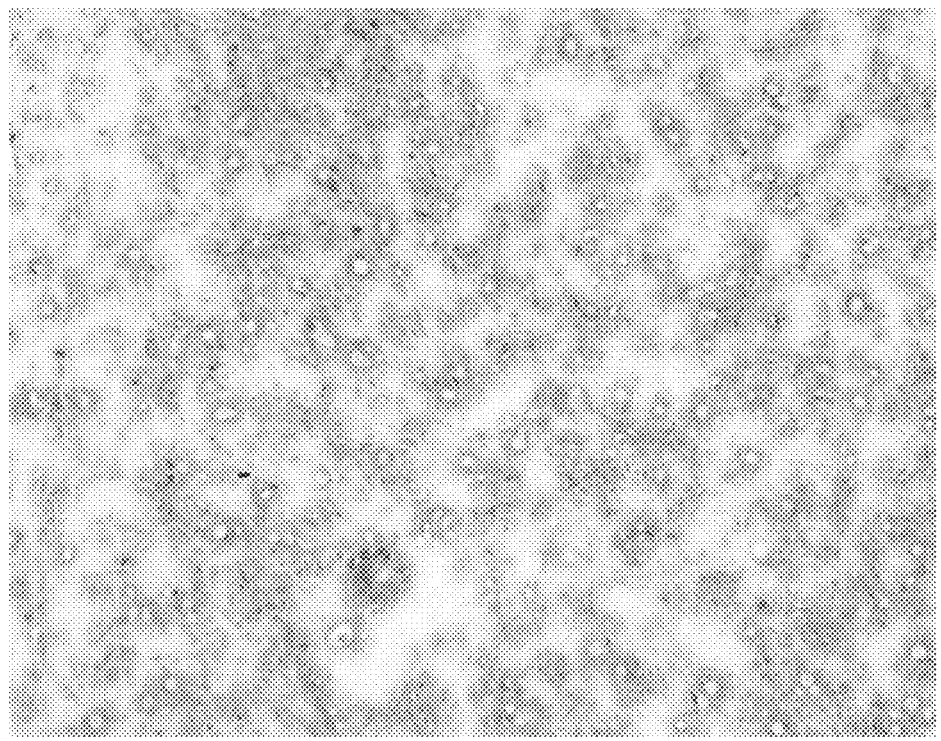
FIG. 15A depicts severe damage to abnormal tissue induced by pulsed ultrasound.
Figure 15B:
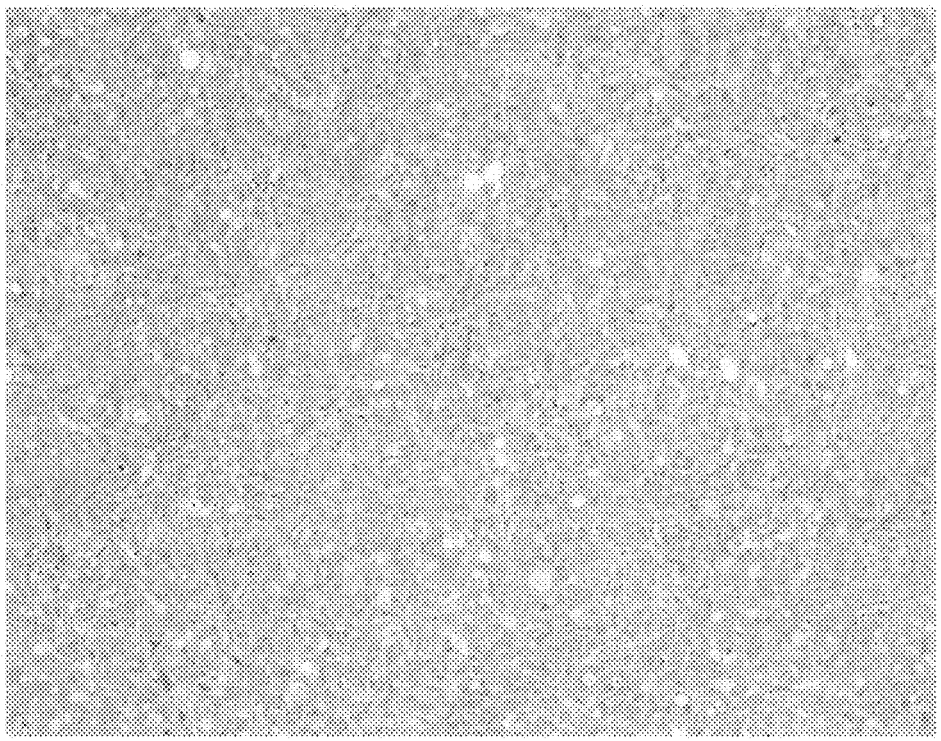
FIG. 15B depicts no damage in non-irradiated (control) part of the abnormal tissue.

FIG. 15A shows severe damage to abnormal tissue in vivo induced by pulsed ultrasound. FIG. 15B shows no damage in non-irradiated (control) part of the abnormal tissue.

Figures 16A, 16B:
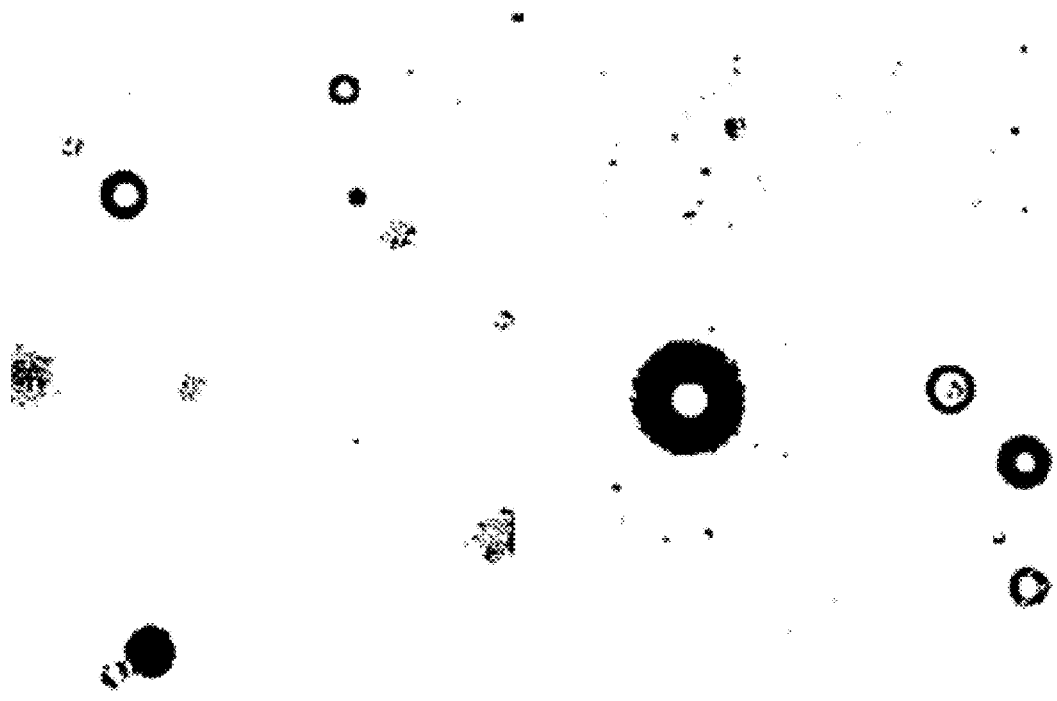
FIGS. 16A&B depict damage induced in heterogeneous tissue phantom by pulsed electromagnetic radiation (near infra-red laser pulses).

FIGS. 16A&b shows damage induced in heterogeneous tissue phantom by pulsed electromagnetic radiation (near infra-red laser pulses). The areas with higher absorption have damage (microbubbles), while the areas with lower absorption do not have the damage. Smaller damaged areas were obtained after irradiation with one pulse at fluence of 1.05 J/cm$^2$ as shown in FIG. 16A compared to larger damaged areas at fluence of 1.4 J/cm$^2$ as shown in FIG. 16B. These data demonstrate that one can induce selective damage to abnormal areas of tissues with pulsed electromagnetic heating of the areas. Moreover, by optimizing the electromagnetic wave parameters, one may control the size of the damaged areas to avoid or minimize damage to normal tissues.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

I claim:

1. A method for fat destruction or removal in a patient comprising:
    injecting particulate enhancing agents that comprise one or more of gold, silver and platinum into an interstitial space in fat tissues to be treated in the patient, and
    applying electromagnetic radiation at one or more frequencies selected from a range of frequencies from and including a radio-frequency energy frequency to and including a near infra-red energy frequency, wherein the particulate enhancing agents absorb the electromagnetic energy and result in heating and destruction of the fat tissues.

2. The method of claim 1, wherein the electromagnetic energy is from and including the radio-frequency energy to and including near infra-red energy and, in the absence of the particulate enhancing agents, a set of parameters including frequency, pulse duration, pulse repetition rate, treatment duration, and amplitude of the electromagnetic radiation in the radio-frequency energy along with mode of radiation—continuous, pulsed, or mixtures thereof—and the field amplitude and mode—continuous, pulsed, variable, or mixtures thereof, are tuned to the fat tissues being treated.

3. The method of claim 1, wherein the electromagnetic energy is radio-frequency energy and one or more parameters of the electromagnetic radiation in the radio-frequency energy range, including frequency, pulse duration, pulse repetition rate, treatment duration, amplitude, and field properties, are tuned to the particulate enhancing agents.

4. The method of claim 1, wherein the particulate enhancing agents comprise particles having a largest dimension of less than 100 μm.

5. The method of claim 1, wherein the particulate enhancing agents comprise particles having a largest dimension of less than 10 μm.

6. The method of claim 1, wherein the particulate enhancing agents comprise particles having a largest dimension of less than 1 μm.

7. The method of claim 1, wherein the particulate enhancing agents comprise particles having a largest dimension of less than 100 nm.

8. The method of claim 1, wherein the particulate enhancing agents comprise particles having a largest dimension of less than 10 nm.

9. The method of claim 1, wherein the particulate enhancing agents comprise particles having a largest dimension of less than 1 nm.

10. The method of claim 1, wherein wearable devices are used to deliver the electromagnetic radiation and thereby provide long duration of treatment in the patient.

11. The method of claim 1, wherein the radio-frequency energy has a frequency between about 2 MHz and 500 MHz.

12. The method of claim 1, wherein the radio-frequency energy has a frequency between about 100 MHz and 500 MHz.

13. The method of claim 1, further comprising applying a pharmaceutical agent or agents to the patient to enhance the destruction and removal of the fat tissues.

14. The method of claim 1, wherein the electromagnetic energy is near-infrared energy.

15. A cosmetic treatment for fat destruction or removal in a fat containing tissue comprising injecting particulate enhancing agents into an interstitial space in the fat containing tissue, and applying electromagnetic radiation at one or more frequencies selected from a range of frequencies from and including a radio-frequency energy frequency to and including an near infra-red energy frequency, wherein the particulate enhancing agents absorb the electromagnetic energy and comprise a metal selected from the group consisting of gold, silver, platinum and combinations thereof.

* * * * *